US011437122B2

(12) United States Patent
Fry et al.

(10) Patent No.: US 11,437,122 B2
(45) Date of Patent: *Sep. 6, 2022

(54) ELECTRONIC METHODS AND SYSTEMS FOR MICROORGANISM CHARACTERIZATION

(71) Applicant: Fry Laboratories, LLC, Scottsdale, AZ (US)

(72) Inventors: Stephen E. Fry, Scottsdale, AZ (US); Jeremy Ellis, Mesa, AZ (US); Matthew Shabilla, Scottsdale, AZ (US)

(73) Assignee: FRY LABORATORIES, LLC, Scottsdale, AZ (US)

( * ) Notice: Subject to any disclaimer, the term of this patent is extended or adjusted under 35 U.S.C. 154(b) by 584 days.

This patent is subject to a terminal disclaimer.

(21) Appl. No.: 16/225,328

(22) Filed: Dec. 19, 2018

(65) Prior Publication Data

US 2019/0147979 A1 May 16, 2019

Related U.S. Application Data

(63) Continuation of application No. 15/630,072, filed on Jun. 22, 2017, now Pat. No. 10,204,209, which is a continuation of application No. 15/411,350, filed on Jan. 20, 2017, now Pat. No. 9,971,867, which is a continuation of application No. 14/197,027, filed on Mar. 4, 2014, now Pat. No. 9,589,101.

(51) Int. Cl.
| | |
|---|---|
| *G01N 33/48* | (2006.01) |
| *G01N 33/50* | (2006.01) |
| *G16B 30/10* | (2019.01) |
| *G16B 30/00* | (2019.01) |
| *G16B 5/00* | (2019.01) |
| *G16B 15/00* | (2019.01) |
| *G16B 20/00* | (2019.01) |
| *G16B 45/00* | (2019.01) |
| *G16B 50/00* | (2019.01) |
| *G16B 20/20* | (2019.01) |

(52) U.S. Cl.
CPC ............. *G16B 30/10* (2019.02); *G16B 5/00* (2019.02); *G16B 15/00* (2019.02); *G16B 20/00* (2019.02); *G16B 20/20* (2019.02); *G16B 30/00* (2019.02); *G16B 45/00* (2019.02); *G16B 50/00* (2019.02)

(58) Field of Classification Search
CPC .......... G16B 30/00; G16B 5/00; G16B 15/00; G16B 20/00; G16B 45/00; G16B 50/00
See application file for complete search history.

(56) References Cited

U.S. PATENT DOCUMENTS

| | | | |
|---|---|---|---|
| 5,849,492 A | 12/1998 | Rogan | |
| 6,023,659 A * | 2/2000 | Seilhamer | ............... G16B 50/00 |
| | | | 702/19 |
| 6,775,622 B1 | 8/2004 | Holloway | |
| 9,589,101 B2 | 3/2017 | Fry et al. | |
| 9,971,867 B2 * | 5/2018 | Fry | ........................ G16B 30/00 |
| 10,204,209 B2 * | 2/2019 | Fry | .......................... G16B 5/00 |
| 2002/0156009 A1 * | 10/2002 | Ballinger | ............. C07K 14/545 |
| | | | 702/190 |
| 2003/0099928 A1 | 5/2003 | Burlage | |
| 2003/0119015 A1 | 6/2003 | Frazer et al. | |
| 2008/0261222 A1 | 10/2008 | Rogan et al. | |
| 2017/0147747 A1 | 5/2017 | Fry et al. | |

FOREIGN PATENT DOCUMENTS

| | | |
|---|---|---|
| DE | 102008019712 | 10/2009 |
| WO | 02063479 | 8/2002 |

OTHER PUBLICATIONS

U.S. Appl. No. 14/197,027, "Final Office Action", dated May 24, 2016, 18 pages.
U.S. Appl. No. 14/197,027, "Non-Final Office Action", dated Jan. 29, 2016, 12 pages.
U.S. Appl. No. 14/197,027, "Notice of Allowance", dated Nov. 23, 2016, 19 pages.
U.S. Appl. No. 15/411,350, "Corrected Notice of Allowance", dated Apr. 2, 2018, 5 pages.
U.S. Appl. No. 15/411,350, "First Action Interview Pilot Program Pre-Interview Communication", dated Mar. 21, 2017, 4 pages.
U.S. Appl. No. 15/411,350, "Notice of Allowance", dated Jan. 18, 2018, 7 pages.
U.S. Appl. No. 15/411,350, "Notice of Allowance", dated May 10, 2017, 7 pages.
U.S. Appl. No. 15/630,072, "First Action Interview Pilot Program Pre-Interview Communication", dated Dec. 7, 2017, 5 pages.
U.S. Appl. No. 15/630,072, "Non Final Office Action", dated May 24, 2018, 13 pages.
U.S. Appl. No. 15/630,072, "Notice of Allowance", dated Sep. 20, 2018, 7 pages.
Agren et al., "Gegenees: Fragmented Alignment of Multiple Genomes for Determining Phylogenomic Distances and Genetic Signatures Unique for Specified Target Groups", PLOS ONE, vol. 7, No. 6, Jun. 18, 2012, 11 pages.
Craig et al., "Ordering of Cosmid Clones Covering The Herpes Simplex Virus Type I (Hsv-I) Genome: A Test Case For Fingerprinting By Hybridisation", Nucleic Acids Research, vol. 18, Issue 9, May 1, 1990, pp. 2653-2660.
EP15758111.7, "Extended European Search Report", dated Aug. 3, 2017, 9 pages.
EP15758111.7, "Office Action", dated Jan. 2, 2019, 9 pages.

(Continued)

*Primary Examiner* — Russell S Negin
(74) *Attorney, Agent, or Firm* — Kilpatrick Townsend & Stockton LLP

(57) ABSTRACT

Systems and methods to characterize one or more microorganisms or DNA fragments thereof are disclosed. Exemplary methods and systems use comparison of DNA sequencing information to information in one or more databases to characterize the one or more microorganism or DNA fragments thereof. Exemplary systems and methods can be used in a clinical setting to provide rapid analysis of microorganisms that may be a cause of infection.

17 Claims, 10 Drawing Sheets

(56) References Cited

OTHER PUBLICATIONS

Gonzalez et al., "Clustering exact matches of pairwise sequence alignments by weighted linear regression", BMC Bioinformatics, Biomed Central, London, GB, vol. 9, No. 1, Feb. 18, 2008, p. 102.
Hasman et al., "Rapid Whole-Genome Sequencing for Detection and Characterization of 1-20 Microorganisms From Clinical Samples", J. Clin. Microbiology vol. 52, No. 1, Jan. 2014, pp. 139-146.
Kostic et al., "PathSeq: software to identify or discover microbes by deep sequencing of human tissue", Nature Biotechnology, vol. 29, No. 5, May 1, 2011, pp. 393-396.
Murata et al., "Simultaneous Comparison of Three Protein Sequences", Proc Natl Acad Sci U S A., vol. 82, May 1985, pp. 3073-3077.
Oldmeadow et al., "Model Selection in Bayesian Segmentation of Multiple DNA Alignments", Bioinformatics, vol. 27, No. 5, Mar. 1, 2011, pp. 604-610.
Oldmeadow et al., "Multiple Evolutionary Rate Classes in Animal Genome Evolution", Mol. Biol. Evol., vol. 27, No. 4, Apr. 2010, pp. 942-953.
PCT/US2015/018533, "International Search Report and Written Opinion", dated Jul. 8, 2015, 9 pages.
Petrosino et al., "Metagenomic Pyrosequencing and Microbial Identification", Clinical Chemistry, vol. 55, No. 5, May 2009, pp. 856-866.
U.S. Appl. No. 15/411,350, Corrected Notice of Allowance, dated Feb. 13, 2018, 5 pages.
Amar et al., "Involvement of Tissue Bacteria in the Onset of Diabetes in Humans: Evidence for a Concept", Diabetologia, vol. 54, No. 12, Dec. 2011, pp. 3055-3061.
Andersson et al., "Comparative Analysis of Human Gut Microbiota by Barcoded Pyrosequencing", Plos One, vol. 3, No. 7, e2836, Jul. 30, 2008, pp. 1-8.
Claesson et al., "Comparison of Two Next-Generation Sequencing Technologies For Resolving Highly Complex Microbiota Composition Using Tandem Variable 16S rRNA Gene Regions", Nucleic Acids Research, vol. 38, No. 22, e200, Sep. 29, 2010, pp. 1-13.
EP15758111.7, Office Action, dated Sep. 3, 2019, 4 pages.
Huson et al., "Megan Analysis of Metagenomic Data", Genome Research, vol. 17, No. 3, Mar. 2007, pp. 377-386.
Knapp et al., "Diet-Related Composition of the Gut Microbiota of Lumbricus Rubellus as Revealed By A Molecular Fingerprinting Technique and Cloning", Soil Biology & Biochemistry vol. 41, No. 11, Nov. 2009, pp. 2299-2307.
Schmeider et al., "Fast Identification and Removal of Sequence Contamination from Genomic and Metagenomic Datasets", PLoS ONE, vol. 6, Issue 3, e17288, Mar. 9, 2011, 11 pages.
Urich et al., "Simultaneous Assessment of Soil Microbial Community Structure and Function Through Analysis of the Meta-Transcriptome", PLoS ONE, vol. 3, No. 6, e2527, Jun. 25, 2008, pp. 1-13.

\* cited by examiner

Complete Significant Contribution:

| Species Name | Close Match | Potential Novel | Total Percent | Match Count | Novel Count | Total Count |
|---|---|---|---|---|---|---|
| Streptococcus intermedius | 65.98 | 0 | 65.98 | 2968 | 0 | 2968 |
| Fusobacterium nucleatum | 28.03 | 0 | 28.03 | 1261 | 0 | 1261 |
| Neisseria lactamica | 4.2 | 0 | 4.2 | 189 | 0 | 189 |

Antibiotic Susceptibility:
Neisseria species:
Active antibiotics for Neisseria include third-generation cephalosporin antibiotics such as cefotaxime and ceftriaxone. Some species have been shown to be resistant to the penicillin family of antibiotics. References: Tunkel AR, Hartman BJ, Kaplan SL, Kaufman BA, Roos KL, Scheld WM, Whitley RJ (November 2004). "Practice guidelines for the management of bacterial meningitis". Clin Infect Dis 39 (9): 1267-84. "UK doctors advised gonorrhoea has turned drug resistant BBC News. 10 October 2011.

Fusobacterium species:
Antibiotic susceptibility varies among Fusobacterium species. Treatment of Fusobacterium infections depends on the site of infections. Antibiotics used to treat Fusobacterium infections include: Metronidazole, piperacillin/tazobactam, ticarcillin/clavulanate, amoxicillin/sulbactum, ampicillin/sulbactum, ertupenem, imipenem, meropenem, clindamycin, and cefoxitin. Some resistance to penicillin noted with widespread resistance to erythromycin and other macrolides. References: Citron, D. M., Poxton, I. R., & Baron, E. J. (2007). Bacteroides, Porphyromonas, Prevotella, Fusobacterium, and Other Anaerobic Gram-Negative Rods. In P. R. Murray, E. J. Baron, M. L. Landry, J. H. Jorgensen & M. A. Pfaller (Eds.), Manual of Clinical Microbiology (9th ed., pp. 911-932). Washington, D.C.: ASM Press. Riordan, T. (2007). Human infection with Fusobacterium necrophorum (Necrobacillosis), with a focus on Lemierre's syndrome. Clinical Microbiology Reviews, 20(4), 622-659. doi:10.1128/CMR.00011-07. Boyanova, L., Kolarov, R., & Mitov, I. (2007). Antimicrobial resistance and the management of anaerobic infections. Expert Review of Anti-Infective Therapy, 5(4), 685-701.

Streptococcus species:
Active antibiotics for Streptococcus include: penicillin, amoxicillin, intramuscular benzathine penicillin G, erythromycin, clindamycin, cephalosporins, cephalexin, cefuroxime axetil, and cefdinir. Penicillin has been reported to be ineffective in some cases. Beta-lactams and macrolides have been reported as an inactive antibiotics. References: Hooton TM. A comparison of azithromycin and penicillin V for the treatment of streptococcal pharyngitis. Am J Med. 1991 Sep 12;91(3A):23S-26S.PubMed. Cohen R, Reinert P, De La Rocque F, Levy C, Boucherat M, Robert M, Navel M, Brahimi N, Deforche D, Palestro B, Bingen E. Comparison of two dosages of azithromycin for three days versus penicillin V for ten days in acute group A streptococcal tonsillopharyngitis. Pediatr Infect Dist J. 2002 Apr;21(4):297-303. Casey JR, Pichichero ME. Meta-analysis of cephalosporin versus penicillin treatment of group A streptococcal tonsillopharyngitis in children. Pediatrics. 2004 Apr;113(4):866-82. Scholz H. Streptococcal-A tonsillopharyngitis: a 5-day course of cefuroxime axetil versus a 10-day course of penicillin V. results depending on the children's age. Chemotherapy. Baltimore RS (February 2010). "Re-evaluation of antibiotic treatment of streptococcal pharyngitis". Curr. Opin. Pediatr. 22 (1): 77-82. Shulman, ST; Bisno, AL; Clegg, HW; Gerber, MA; Kaplan, EL; Lee, G; Martin, JM; Van Beneden, C (2012 Sep 9). "Clinical Practice Guideline for the Diagnosis and Management of Group A Streptococcal Pharyngitis: 2012 Update by the Infectious Diseases Society of America.". Clinical infectious diseases : an official publication of the Infectious Diseases Society of America. Choby BA (March 2009). "Diagnosis and treatment of streptococcal pharyngitis" Am Fam Physician 79 (5): 383-90. Albrich, W; Monnet, DL, Harbarth, S (2004). "Antibiotic selection pressure and resistance in Streptococcus pneumoniae and Streptococcus pyogenes". Emerging Infect. Dis. 10 (3): 514-7. PMC 3322805. PMID 15109425.

FIG. 6

ELECTRONIC METHODS AND SYSTEMS FOR MICROORGANISM CHARACTERIZATION

CROSS-REFERENCE TO RELATED APPLICATIONS

The present application is a continuation of U.S. application Ser. No. 15/630,072, filed on Jun. 22, 2017, which is a continuation of U.S. application Ser. No. 15/411,350, filed on Jan. 20, 2017, now issued as U.S. Pat. No. 9,971,867 on May 15, 2018, which is a continuation of U.S. application Ser. No. 14/197,027, filed on Mar. 4, 2014, now issued as U.S. Pat. No. 9,589,101 on Mar. 7, 2017. Each of these applications is hereby incorporated by reference in its entirety for all purposes.

BACKGROUND

1. Technical Field

The present disclosure generally relates to electronic methods and systems for characterizing one or more microorganisms or DNA fragments thereof. More particularly, the disclosure relates to methods and systems for characterizing one or more microorganisms or DNA fragments thereof based on a comparison of microorganism DNA information with information in one or more databases.

2. Background Art

Characterizing microorganisms may be desirable for several reasons. For example, it may be desirable to characterize or identify one or more microorganisms or microorganism species that is or is thought to be a cause of infection in an animal. If the microorganisms or species are known, such information may be used to treat the animal.

Computerized systems and methods that have an ability to identify a specific pathogenic microorganism have been developed. Such presently existing products, however, generally require significant processing time, e.g., on the order of several days, making the use of such systems impractical in clinical applications, because by the time any results are obtained, the infection may no longer be treatable. In addition, results obtained by such currently available software packages may not be useful to doctors or other health care professionals, because the results may require additional software or specially trained researchers to interpret the results of the microorganism identification, to manually determine a suitable course of treatment, and to obtain therapy resistance information associated with the microorganism for use by the physician in recommending a treatment. In addition, such systems may only identify one microorganism or species at a time, and information for the particular microorganism generally must be stored in a database. In other words, the methods and systems generally cannot identify or characterize microorganisms that have not previously been identified and that do not have associated information stored in a database.

Accordingly, improved electronic methods and systems for characterizing or identifying one or more microorganisms in an efficient manner are desired. The methods and systems preferably do not require an Internet connection for an extended period of time.

SUMMARY OF THE DISCLOSURE

Various embodiments of the present disclosure relate to electronic systems and methods that can be used to characterize or identify one or more microorganisms. While the ways in which various embodiments of the present disclosure address drawbacks of prior systems and methods are discussed in more detail below, in general, various embodiments of the disclosure provide systems and methods that can characterize and/or identify one or more microorganisms in a relatively short amount of time. Exemplary methods and systems can evaluate a plurality of microorganisms at the same time or in parallel to further reduce the time associated with identification or characterization of multiple microorganisms. The exemplary methods and systems can be used to characterize one or more types of microorganisms, such as bacteria, fungi, protozoa, and viruses and/or one or more species of microorganisms within one or more types of microorganisms. Because the microorganisms can be characterized or identified in a relatively short amount of time, exemplary systems and methods described herein are suitable for clinical applications, where rapid identification of the microorganism(s) is desired. Further, exemplary methods and systems can provide care givers with suggested treatments and/or sensitivity and/or treatment resistance information relating to various treatments for the characterized or identified microorganism(s) in an easy to read and interpret manner. As used herein characterized or identified microorganisms can refer to a genus or a species of the characterized or identified microorganism(s) or to the microorganism itself.

In accordance with exemplary embodiments of the disclosure, one method of characterizing one or more microorganisms includes the step of selecting, by a computer, a digital file comprising one or more digital DNA sequences, wherein each of the one or more digital DNA sequences corresponds to a microorganism to be characterized; segmenting, by the computer, each of the one or more digital DNA sequences into one or more first portions; performing, by the computer, a set of alignments by comparing the one or more first portions to information stored in a first database; determining, by the computer, sequence portions from among the one or more first portions that have an alignment match to the information stored in the first database; optionally further segmenting, by the computer, each of the one or more digital DNA sequences into one or more second portions; performing, by the computer, a set of alignments by comparing the one or more first portions or the one or more second portions to information stored in a second database; determining, by the computer, sequence portions from among the one or more first portions or the one or more second portions that have an alignment match to the information stored in the second database; and characterizing one or more microorganisms or DNA fragments thereof based on the alignment match to the information stored in one or more of the first database and the second database.

Methods in accordance with various aspects of the disclosure can be used to characterize multiple microorganisms simultaneously or in parallel, such that multiple microorganisms can be identified in a relatively short amount of time—e.g., in less than forty-eight or less than twenty-four hours.

Methods in accordance with further exemplary aspects of the disclosure include the steps of further segmenting, by the computer, each of the one or more digital DNA sequences into one or more second portions; performing, by the computer, a set of alignments by comparing the one or more second portions to information stored in at least one database (which may include the second database); and determining, by the computer, sequence portions from among the one or more second portions that have an alignment match to information stored in the at least one database can be repeated a number (n) times. In accordance with these embodiments, a comparison window may be used to evaluate whether there is a match and can decrease as n increases. The DNA portions can be compared to information within the first, second, or another database using, for example, one or more of BLAST, OTU, G-BLASTN, mpiBLAST, BLASTX, PAUDA, USEARCH, LAST, and BLAT, or suitable other techniques.

The first and second portions noted herein can be the same or different. And, one or more first portions may have the same length (e.g., same number of base pairs) or different lengths. Similarly, one or more second portions may have the same length or different lengths. In accordance with these embodiments, a first database can include information for a particular type of microorganism, such as for bacteria, fungi, protozoa, or viruses. A second database can be a comprehensive nucleic acid database that includes a larger selection of information, such as information relating to two or more types of microorganisms. The information in the databases can include nucleic acid information, such as DNA and/or RNA information corresponding to the respective microbes.

Exemplary methods can be automatic. For example, one or more or all of the process steps can be automatically performed by the computer. Exemplary methods can also include a step of detecting, by the computer, an in-process sequence run and querying a server upon completion of the sequence run to retrieve a completed digital file. Exemplary methods can also include a step of generating a report, including the one or more characterized microorganism(s) based on the alignment match to the information stored in one or more of the first database and the second database. The report can include corresponding treatment(s) for an infection including the one or more microorganisms and patient sensitivity information for the treatment(s). As used herein, "match" can refer to a threshold number or percent of base pairs that match. For example, a 100% match or another threshold level of match.

In accordance with further exemplary embodiments of the disclosure, an article of manufacture including a non-transitory computer readable medium having instructions stored thereon that, in response to execution by a computing device, cause the computing device to perform operations comprising the method steps described herein.

In accordance with further exemplary embodiments of the disclosure, a method of automatically characterizing one or more microorganisms can be performed using one or more databases. Exemplary methods include the steps of detecting a sequence run that generates a digital DNA sequence of one or more microorganisms; selecting, by a computer, a digital file comprising one or more digital DNA sequences, wherein each of the one or more digital DNA sequences corresponds to a microorganism to be characterized; segmenting, by the computer, each of the one or more digital DNA sequences into one or more portions; performing, by the computer, a set of alignments by comparing the one or more portions to information stored in one or more databases; determining, by the computer, sequence portions from among the one or more portions that have an alignment match to the information stored in the one or more databases; and characterizing one or more microorganism(s) or DNA fragments thereof based on the alignment match. In accordance with various aspects of these embodiments, the method can be used to characterize multiple microorganisms simultaneously or in parallel, such that multiple microorganisms can be identified in a relatively short amount of time—e.g., in less than forty-eight or less than twenty-four hours. In accordance with further exemplary aspects, the method includes the steps of further segmenting, by the computer, each of the one or more digital DNA sequences into one or more second portions; performing, by the computer, a set of alignments by comparing the one or more second portions to information stored in at least one database (which may be a second database); and determining, by the computer, sequence portions from among the one or more second portions that have an alignment match to information stored in the at least one database; these steps can be repeated a number (n) times. In these cases, a comparison window that is used to evaluate whether there is a match can decrease as n increases. The DNA portions can be compared to information within at least one database using, for example, one or more of BLAST, OTU, G-BLASTN, mpiBLAST, BLASTX, PAUDA, USEARCH, LAST, and BLAT, or other suitable techniques. If more than one set of portions is used, the first and second portions noted herein can be the same or different. And, one or more first portions may have the same length (e.g., same number of base pair) or different lengths. Similarly, when used, one or more second portions may have the same length or different lengths. In accordance with these embodiments, a first database can include information for a particular type of microorganism, such as for bacteria, fungi, protozoa, or viruses. A second database can be a comprehensive nucleic acid database that includes a larger selection of information, such as information relating to two or more types of microorganisms. The information in the databases can include nucleic acid information, such as DNA and/or RNA information corresponding to the respective microbes. Exemplary methods can also include a step of generating a report, including the one or more microorganism(s) based on the alignment match to the information stored in one or more databases. The report can include corresponding treatment(s) for an infection including the one or more microorganisms and patient sensitivity information for the treatment(s). The foregoing and other aspects, features, and advantages will be apparent from the Detailed Description of Exemplary Embodiments of the Disclosure, the Drawing Figures, and the Claims.

BRIEF DESCRIPTION OF THE DRAWING FIGURES

A more complete understanding of exemplary embodiments of the present disclosure can be derived by referring to the detailed description and claims when considered in connection with the following illustrative figures.

FIGS. 5 and 6 illustrate examples of information output in an exemplary report generated in accordance with exemplary embodiments of the disclosure.

It will be appreciated that elements in the figures are illustrated for simplicity and clarity and have not necessarily been drawn to scale. For example, the dimensions of some of the elements in the figures may be exaggerated relative to other elements to help to improve the understanding of illustrated embodiments of the present disclosure.

DETAILED DESCRIPTION OF EXEMPLARY EMBODIMENTS

The description of exemplary embodiments provided below is merely exemplary and is intended for purposes of illustration only; the following description is not intended to limit the scope of the disclosure or the claims. Moreover, recitation of multiple embodiments having stated features is not intended to exclude other embodiments having additional features or other embodiments incorporating different combinations of the stated features.

The following disclosure provides systems and methods for characterizing one or more microorganisms that may be utilized on a traditional or mobile computerized interfaces or network capable of providing the disclosed processing, querying, and displaying functionalities. Various examples of the disclosed systems and methods may be carried out through the use of one or more computers, processors, servers, databases, and the like. Various examples disclosed herein provide highly efficient computerized systems and methods for characterizing one or more microorganisms or DNA fragments thereof, such as for example, pathogenic microorganisms in an efficient and timely manner, such that the systems and methods are suitable for use in clinical settings. Exemplary systems and methods can also provide treatment and/or treatment sensitivity information related to the one or more identified microorganism, such that a care provider can use such information.

Figure 1:
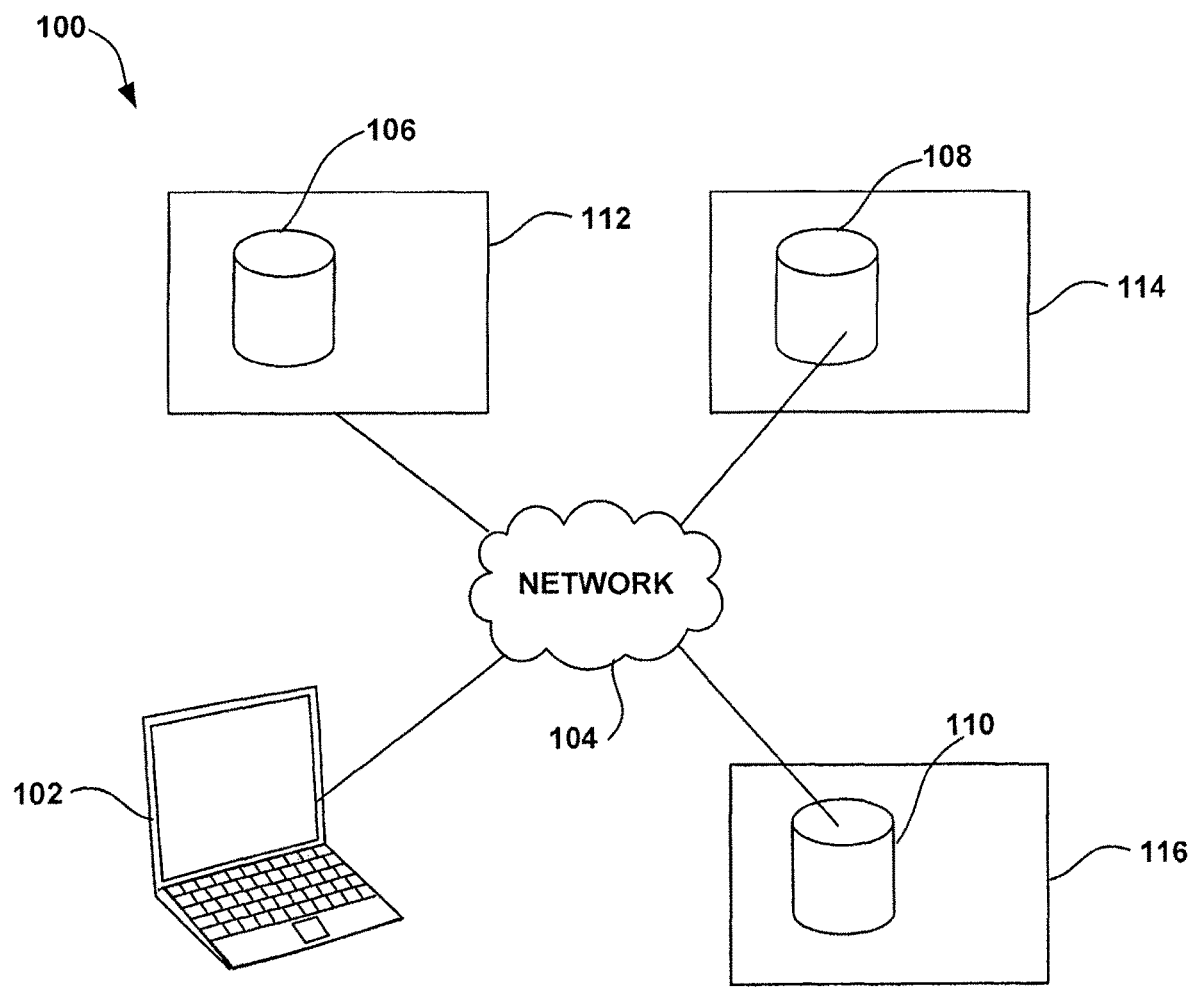
FIG. 1 illustrates a system in accordance with various embodiments of the disclosure.

FIG. 1 illustrates a system 100 in accordance with exemplary embodiments of the disclosure. As illustrated, system 100 includes a computer 102, which can be connected to a network 104. System 100 can also include one or more databases 106-110, which may form part of one or more servers, such as servers 112-116. Although illustrated as part of separate servers, databases 106-110 can form part of the same server or part of a computer, such as computer 102 or another computer.

Computer 102 can include any suitable devices that perform the computer functions noted below. For example, computer 102 can be or include a desktop computer, notebook computer, workstation, network computer, personal data assistant, minicomputer, mainframe computer, server, supercomputer, mobile device, a wearable computer, a sequencing (e.g., DNA sequencing) device, or other device having suitable computing capabilities.

Network 104 can be or include a local area network (LAN), a wide area network, a personal area network, a campus area network, a metropolitan area network, a global area network, or the like. Network 104 can be coupled to one or more computers 102, servers 112-116, other networks, and/or other devices using an Ethernet connection, other wired connections, a WiFi interface, other wireless interfaces, or other suitable connection.

Servers 112-116 can include any suitable computing device, including devices described above in connection with computer 102. Similarly, databases 106-110 can include any suitable database, such as those described in more detail below.

Figure 2:
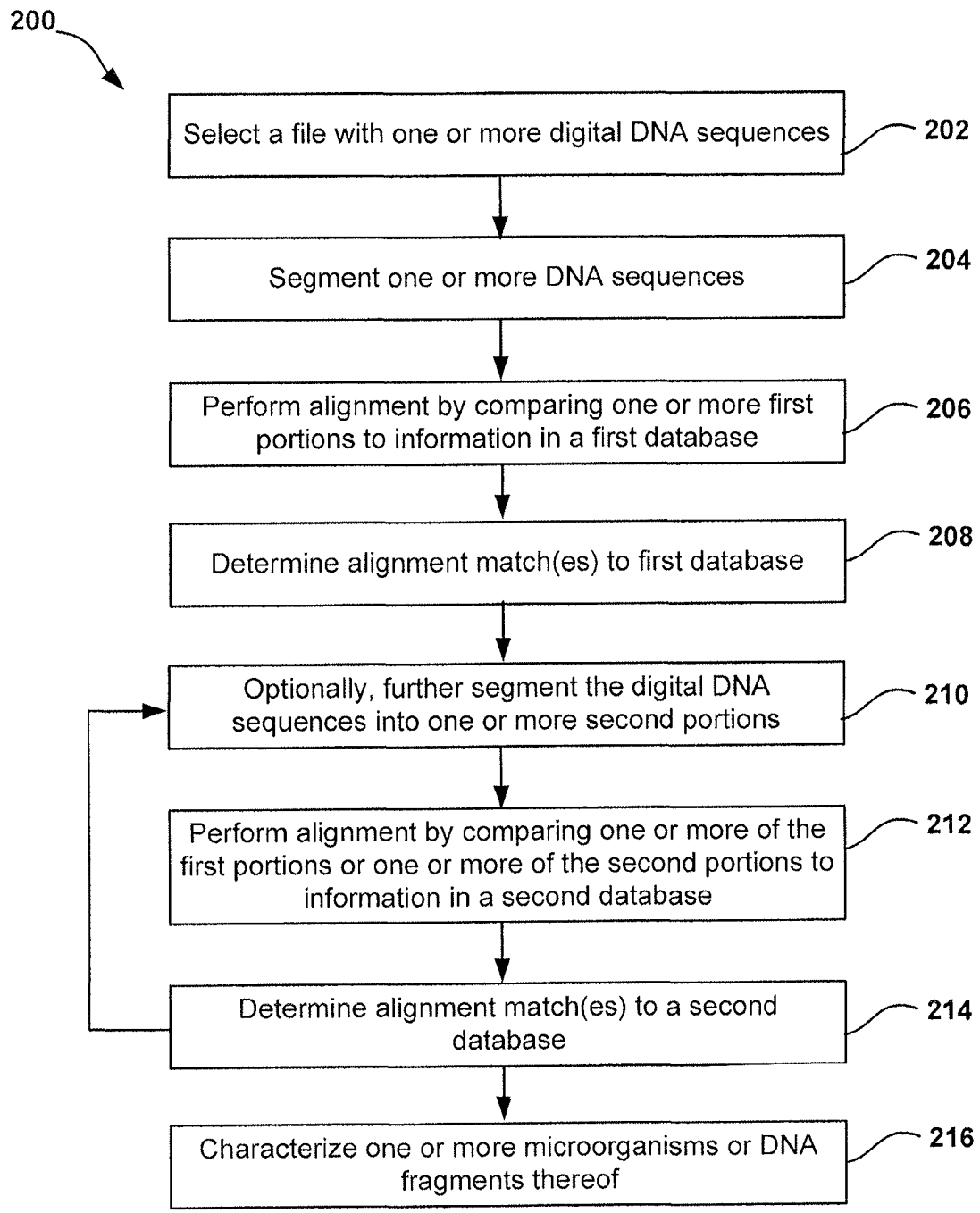
FIG. 2 illustrates a method in accordance with exemplary embodiments of the disclosure.

FIG. 2 illustrates a method 200 of characterizing one or more microorganisms in accordance with various examples of the disclosure. Method 200 includes the steps of selecting, by a computer, a digital file comprising one or more digital DNA sequences, wherein each of the one or more digital DNA sequences corresponds to a microorganism to be characterized (step 202); segmenting, by the computer, each of the one or more digital DNA sequences into one or more first portions (step 204); performing, by the computer, a set of alignments by comparing the one or more first portions to information stored in a first database (step 206); determining, by the computer, sequence portions from among the one or more first portions that have an alignment match to the information stored in the first database (step 208); optionally further segmenting, by the computer, each of the one or more digital DNA sequences into one or more second portions (step 210); performing, by the computer, a set of alignments by comparing the one or more first portions or the one or more second portions to information stored in a second database (step 212); determining, by the computer, sequence portions from among the one or more first portions or the one or more second portions that have an alignment match to the information stored in the second database (step 214); and characterizing one or more microorganisms or DNA fragments thereof based on the alignment match to the information stored in one or more of the first database and the second database (step 216). Each of the steps can be performed using, for example, computer 102 of system 100.

Figure 3:
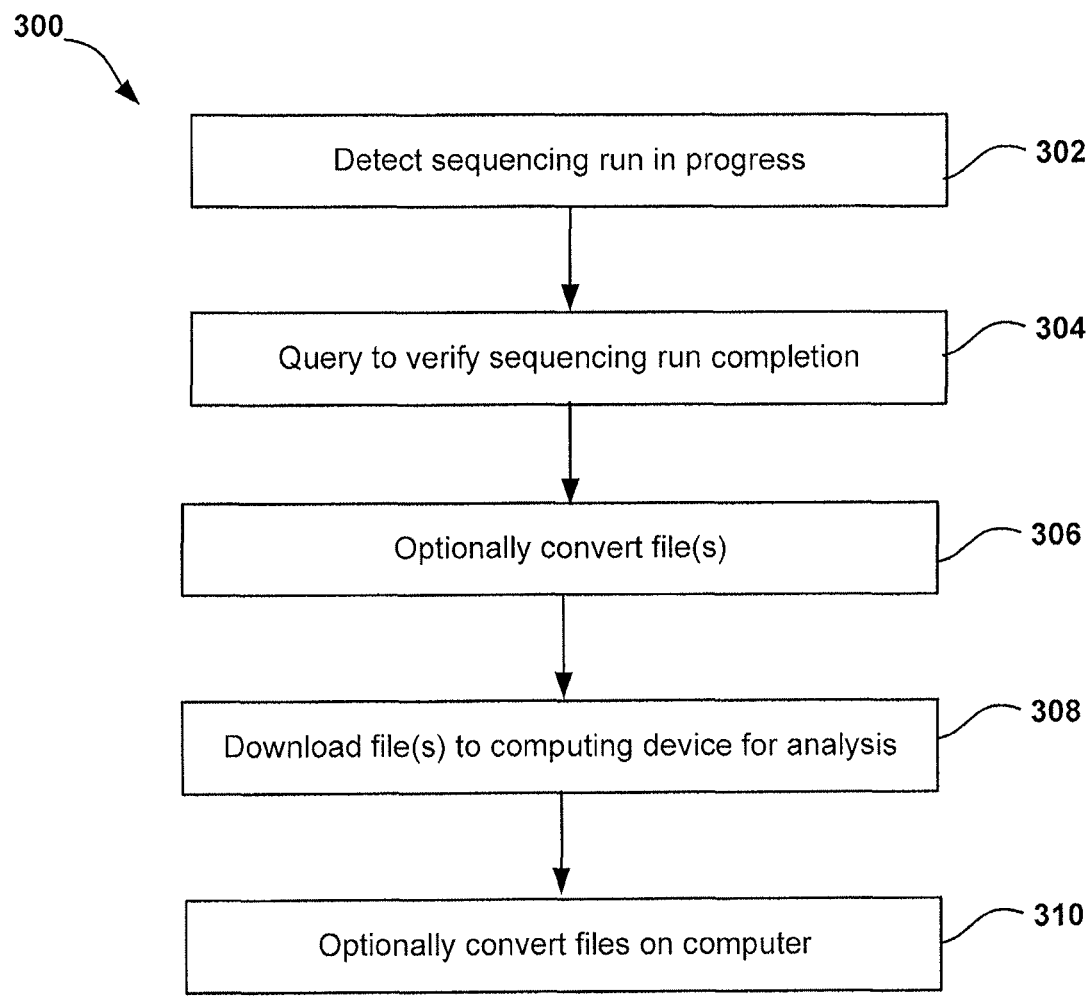
FIG. 3 illustrates a method for automatic sequencing run acquisition in accordance with further exemplary embodiments of the disclosure.

In accordance with some examples of these embodiments, method 200 may also include a step of automatically detecting a sequence run prior to step 202. FIG. 3 illustrates an exemplary sequence run and detection process 300 suitable for use with method 200 and for method 400, described below. In a situation in which a genetic sequencing run is in progress, an in-progress run may be detected—e.g., by a computer (step 302). In response to the detection, the computer may query, for example, a server (e.g., on of servers 112-116) or other computing device on which the sequencing process is occurring to verify completion of the sequencing run (step 304). While it is contemplated that any appropriate file format may be used, in some implementations, the processed sequence file may optionally be converted from one format to another (step 306). For example, an original file may be in a BAM format which can then be converted to a FASTQ file format for further processing and/or data manipulation. Alternatively, the processed sequence file may be in an SFF, FASTQ, or any other appropriate format that is convertible to a FASTQ file format. The file(s) can then be downloaded or otherwise transferred to a computing device for further analysis (step 308), such as for use with method 200. Alternatively, method 200 can employ a sequence file that is, e.g., in FASTQ or other appropriate format from a previously completed sequencing run. Regardless of whether a file is manually selected by a user or automatically detected by the computing device in accordance with FIG. 3, an implementation of the method may then convert the FASTQ or other file format into one or more easily usable FASTA formatted or other appropriately formatted files, illustrated as step 310 in FIG. 3. During step 310, during the file conversion, the sequencing device type and/or the microorganism type can be detected. This allows the method (e.g., method 200 or 400) to automatically process the sequences based on an incoming data (e.g., for a sequencer type) and/or microorganism type.

Referring again to FIG. 2, during step 202, a digital file comprising one or more digital DNA sequences is selected. The digital file can include a plurality of DNA sequences from the one or more files (e.g., FASTA files) that can comprise a predetermined number of base pairs (bp) or otherwise have a predetermined length. In some implementations, 100 bp may be a preferred number of base pairs at which to set this selection threshold, however, any other number of base pairs that allows for adequate processing and elimination of sequence portions that are unlikely to lead to meaningful analysis may also be selected. For example, 50 base pairs, 100 base pairs, or greater than 100 base pairs.

During step 204, the selected DNA sequence file(s) are segmented into one or more first portions, which may be of equal size or length. While any number of (e.g., equal) portions may be used, in some implementations, it may be desirable to match the number of portions to the number of processing cores to be used by a system for processing. For example, when using an analysis computer that has 32 cores, it may be desirable to use 30 of those cores for processing while keeping the remaining two cores in reserve for data management and other processing functions. By way of particular example, it may then be preferable to divide the (e.g., FASTA) sequence file into 30 equal portions, such that one portion of the file may be processed by each desired processing core.

Once the division of one or more digital DNA sequences into one or more first portions is complete, a set of alignments is performed by comparing the one or more first portions to information stored in a first database (step 206). The alignments can be performed using a variety of techniques, including Basic Local Alignment Search Tool (BLAST), OTU, G-BLASTN, mpiBLAST, BLASTX, PAUDA, USEARCH, LAST, BLAT, and other suitable techniques for computational comparison of DNA sequences.

The first database (e.g., one of databases 106-110) can include a database that includes nucleic acid information (e.g., DNA and/or RNA information) corresponding to one or more types of microorganism—e.g., bacteria, viruses, protozoa, or fungi. By way of examples, the first database can include a bacterial nucleic acid database, such as a 16S Microbial DNA Database.

By way of particular examples, step 206 can include performing a set of alignments using BLAST by comparing each of the sequence file portions to a DNA database of 16S rRNA Sequences (Bacteria and Archaea) (hereinafter referred to as "16S"), such as the National Center for Biotechnology Information (NCBI) 16S Microbial database.

The alignments may in some implementations occur substantially simultaneously. It may also be preferable to perform the alignments during step 206 using a relatively small comparison window (e.g., 10 or 11 bp) as the first database may be relatively small and thus, the processing time does not become prohibitive even with relatively small comparison windows. Although not illustrated, method 200 can include collating the aggregate results and eliminating any duplicates present. This may be done, for example, when the alignments are complete at step 206.

During step 208, a computer determines sequence portions from among the one or more first portions that have an alignment match to the information stored in the first database. The step of determining may be based on a predetermined criteria or tolerance for a match.

During step 210, each of the one or more digital DNA sequences from step 202 are optionally further segmented into one or more second portions. Step 210 can be performed in substantially the same way as step 204. During this optional step, the sequence files can be divided into a second plurality of sequence portions, which may be of equal size and/or the number of portions may be determined by a preferred number of processing cores to be used. In accordance with some exemplary embodiments, the second portions differ or are exclusive of the first portions.

During step 212, a set of alignments by comparing the one or more first portions or the one or more second portions (if optional step 210 is performed) to information stored in a second database is performed. Step 212 is similar to step 206, except either first portions or second portions are compared to a second database.

The second database may be relatively large relative to the first database. As such, to reduce processing time, it may be desirable to use a comparison window that is relatively large (e.g., 65 bp, 100 bp, or the like), especially for a first run of step 212. The second database can be or include, for example, a comprehensive nucleic acids database, such as a comprehensive DNA database, a comprehensive RNA database, a eukaryotic DNA database, an NT database, a fungi DNA database, a protozoa DNA database, a comprehensive bacterial database, or a viral nucleic acids database.

As shown in FIG. 2, steps 210-214 can be repeated—e.g., in an iterative manner, wherein a comparison window for determining a match decreases as the number (n) of runs increases. For example, the initial comparison window size can start at 65 bp, and decrease to 40 bp, 25 bp, 10 bp with subsequent runs.

The alignment results from step 212 can be collated and any duplicates removed. The results can then be checked to determine if all of the sequence file portions were aligned through the running of the alignments.

Step 214 can be performed in a manner similar to or the same as step 208. If the alignments performed on the second portions are done using a large comparison window, the results of these alignments may not produce a match between the sequence of the file portion and the second database, due to the low level of stringency. If there are any of the sequence file portions for which the alignment did not identify a match within the second database, a size of a comparison window can be adjusted (e.g., automatically) to increase the stringency—i.e., decrease a size of a comparison window—of a subsequent alignment. The previously unidentified sequence portions are then passed iteratively back into the file segmentation stage 210 where they may then be segmented into any desired number of (e.g., equally) sized sequence portions and alignments are then run for each of the portions. These steps may be iteratively repeated and the stringency increased (comparison window size decreased) each time step 212 is performed and fails to produce a resulting match in step 214. By starting with a lower stringency (e.g., large comparison window) and increasing the stringency (e.g., decreasing the comparison window)—e.g., in a manner that is directly proportional to the number of times which a portion of the sequence has passed through an alignment and failed to find a match, significant processing time may be saved. For example, beginning with a low stringency having a comparison window of 65 bp and then iteratively increasing the stringency by decreasing the comparison window to, for example, 40 bp, 25 bp, and finally 10 bp rather than simply running all of the second database alignments with a comparison window of 10 bp from the start may reduce processing time by many hours or even days. The method may also utilize a maximum stringency (minimum comparison window size) setting in which any leftover sequence portions that have not resulted in a second database match after having been aligned at the highest designated stringency level are discarded to prevent unnecessary processing from continuing.

Table 1 below illustrates the effect of window size on speed and rate at which sequences are characterized in addition to the ratio of contaminating human sequences vs the target microbial sequences.

TABLE 1

| Comparison Window Size | % Recovery | Time (min) | Human | NonHuman | Seq/Min | %/Min | Human/Non-Human |
|---|---|---|---|---|---|---|---|
| 200 | 13.4% | 2.7 | 11500 | 57 | 4344.7 | 5.1% | 201.8 |
| 150 | 35.7% | 4.4 | 30538 | 148 | 7022.0 | 8.2% | 206.3 |
| 100 | 63.5% | 4.7 | 54231 | 311 | 11679.2 | 13.6% | 174.4 |
| 90 | 71.9% | 4.7 | 61433 | 376 | 13039.9 | 15.2% | 163.4 |
| 80 | 79.4% | 5.3 | 67848 | 422 | 12832.7 | 14.9% | 160.8 |
| 75 | 85.2% | 4.7 | 72811 | 466 | 15524.8 | 18.1% | 156.2 |
| 70 | 88.6% | 4.8 | 75222 | 920 | 15896.0 | 18.5% | 81.8 |
| 65 | 90.5% | 4.9 | 76724 | 1026 | 15932.4 | 18.5% | 74.8 |
| 64 | 90.8% | 5.0 | 76991 | 1041 | 15606.4 | 18.2% | 74.0 |
| 63 | 91.4% | 5.4 | 77481 | 1064 | 14681.3 | 17.1% | 72.8 |
| 62 | 91.9% | 5.0 | 77917 | 1096 | 15834.3 | 18.4% | 71.1 |
| 60 | 92.6% | 5.8 | 78472 | 1146 | 13822.6 | 16.1% | 68.5 |
| 50 | 96.0% | 5.8 | 81078 | 1460 | 14304.7 | 16.6% | 55.5 |
| 40 | 98.6% | 8.8 | 82945 | 1849 | 9592.1 | 11.2% | 44.9 |
| 25 | 99.9% | 48.7 | 83349 | 2508 | 1763.7 | 2.1% | 33.2 |

At step 216, one or more microorganisms are characterized. The characterization can include identifying the one or more microorganisms or finding a close match of an unknown microorganism to a known or unknown microorganism in a database.

Exemplary methods can also include a comparison of results from the two alignments determination steps 208 and 214. For example, once collation and removal of duplicate results has been accomplished for both the first database alignments results and the second database (optionally iteratively performed) aligned results, the results of the two databases alignments can be compared. In some implementations of the method, the first database alignment results may first be examined to determine if there are any complete, or 100%, matches. If so, these are assumed to be correctly identified microorganisms due to their high degree of matching and can be placed into a first list. The first database results can then re-analyzed to find matches having a slightly lesser degree of completeness, but for which there is still a reasonably high probability that the microorganism has been correctly identified and these results are also added to the first list. For example, the matches can be 100%, 98%, 97%, 95%, or 90%. For the remaining first database results that fall below the predetermined threshold of reliability for the results to become a member of the first list, a comparison can made with the corresponding second database results for each particular sequence portion to determine whether the second database result (e.g., a match during step 214) or the first database result (from step 208) provides a closer match. In some implementation, this may be accomplished by comparing one or more variables, such as for example, one or more of a percentage identity and sequence E-value, to determine which of the two database alignments result in the closest match. Once it is determined which is the closer match, the results can further analyzed to characterize and/or identify any of the closest matches that do not fall above a predetermined threshold (e.g., 100%, 98%, 97%, 95%, and 90%) of certainty and these results may be categorized as results that do not correspond with the characterized microorganism(s).

A quality of the results of comparisons of matches from steps 208 and 214 can be checked by limiting the analysis to sequence portions that have a predetermined length. For example, either a minimum threshold for sequence length could be set such as, for example, a minimum sequence length of 100 bp, or the results may be limited such that only those above which fall into a certain percentage of the longest sequences, for example, the top 100%, 50%, 30%, 20%, 15%, or 10% of all run sequence lengths may be selected on which to base the remaining analysis. By way of one example, the top 8.6% of sequence lengths can be used. The results can then be tabulated to determine how many matches correspond to each characterized or identified microorganism and any region information can also be tabulated to determine the number of matches for each region analyzed.

Figure 5:
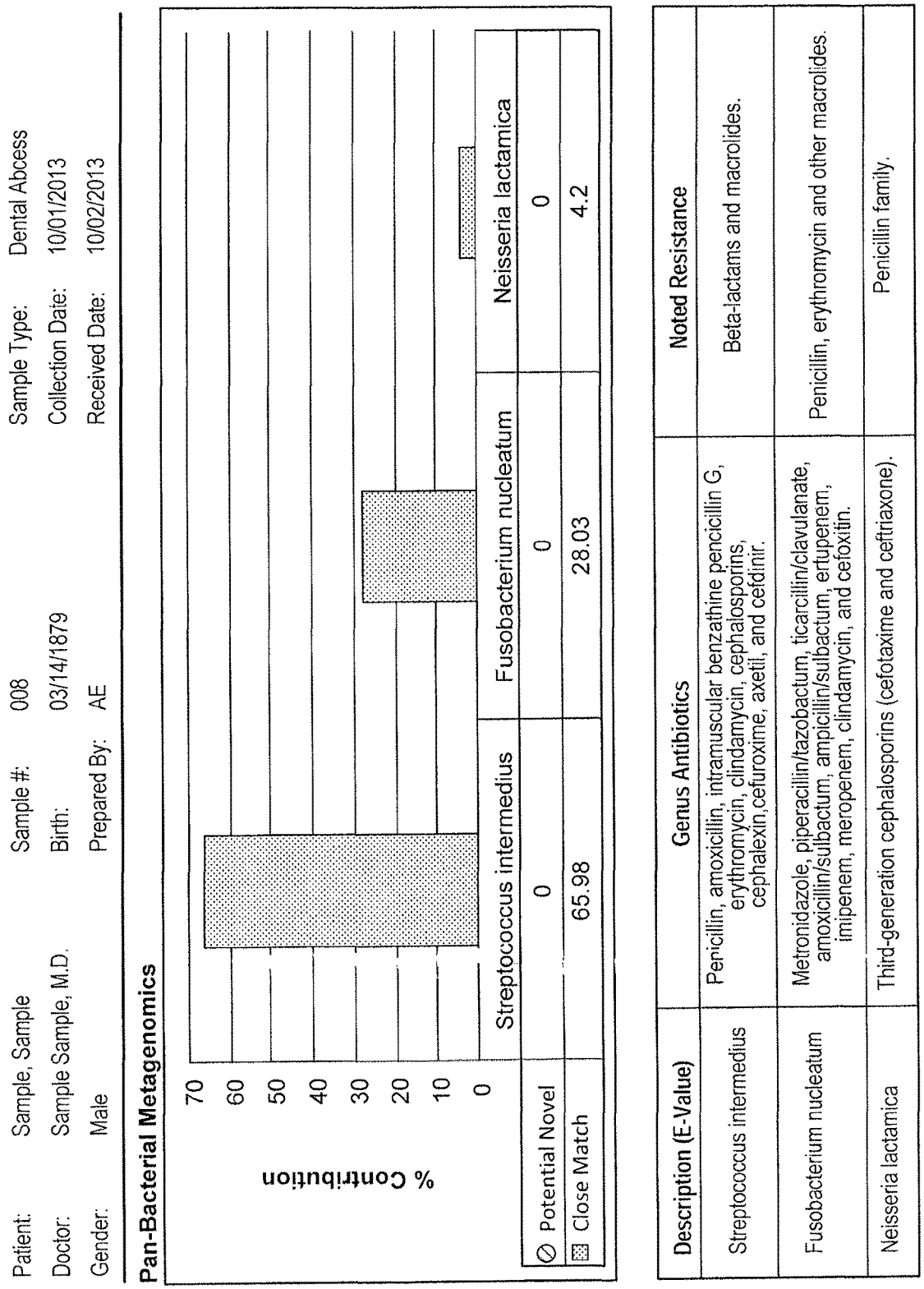
Figure 7:
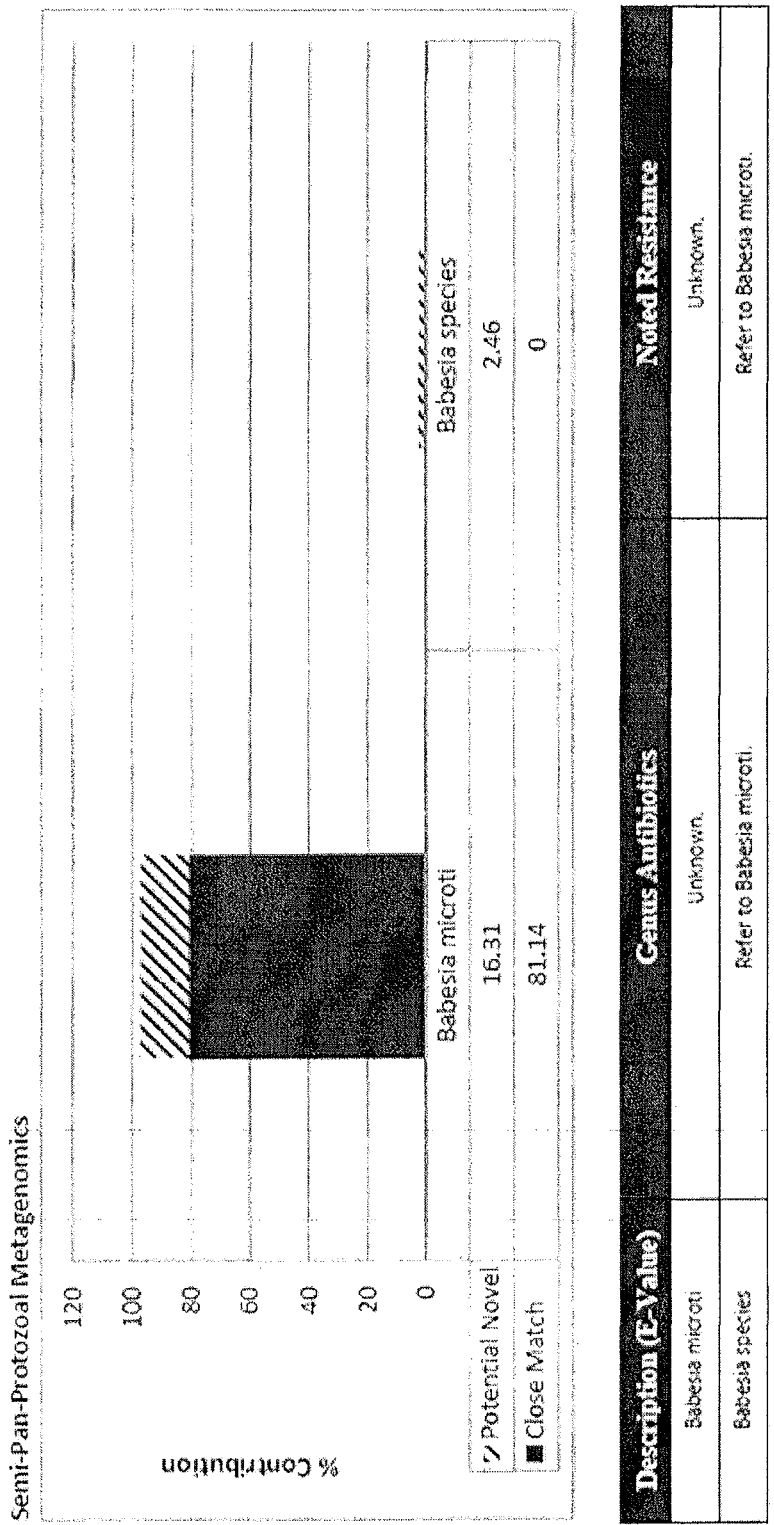
FIGS. 7-10 illustrate results of a computer-based genomics analysis is accordance with further exemplary embodiments of the disclosure.
Figure 8:
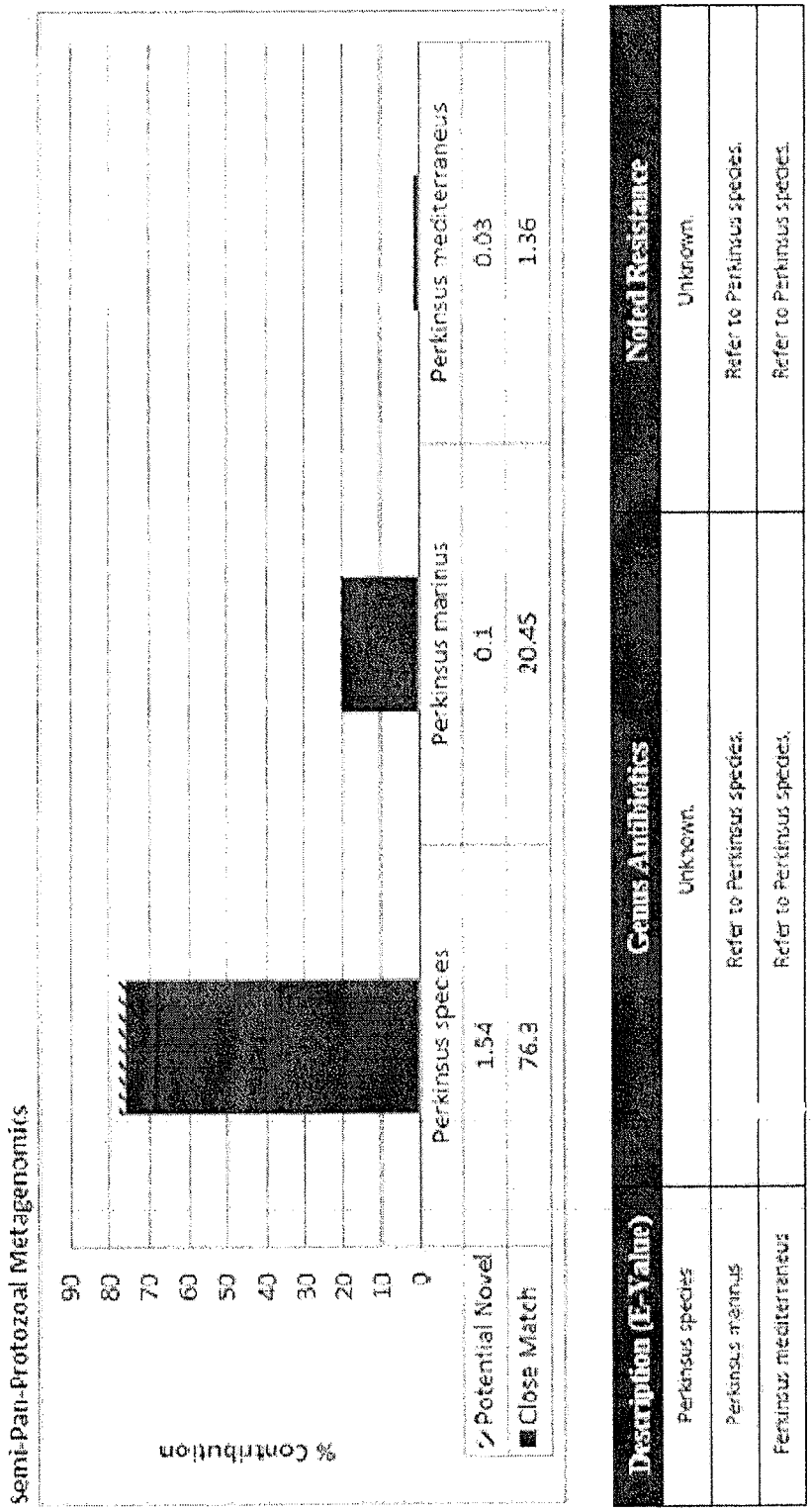
Figure 9:
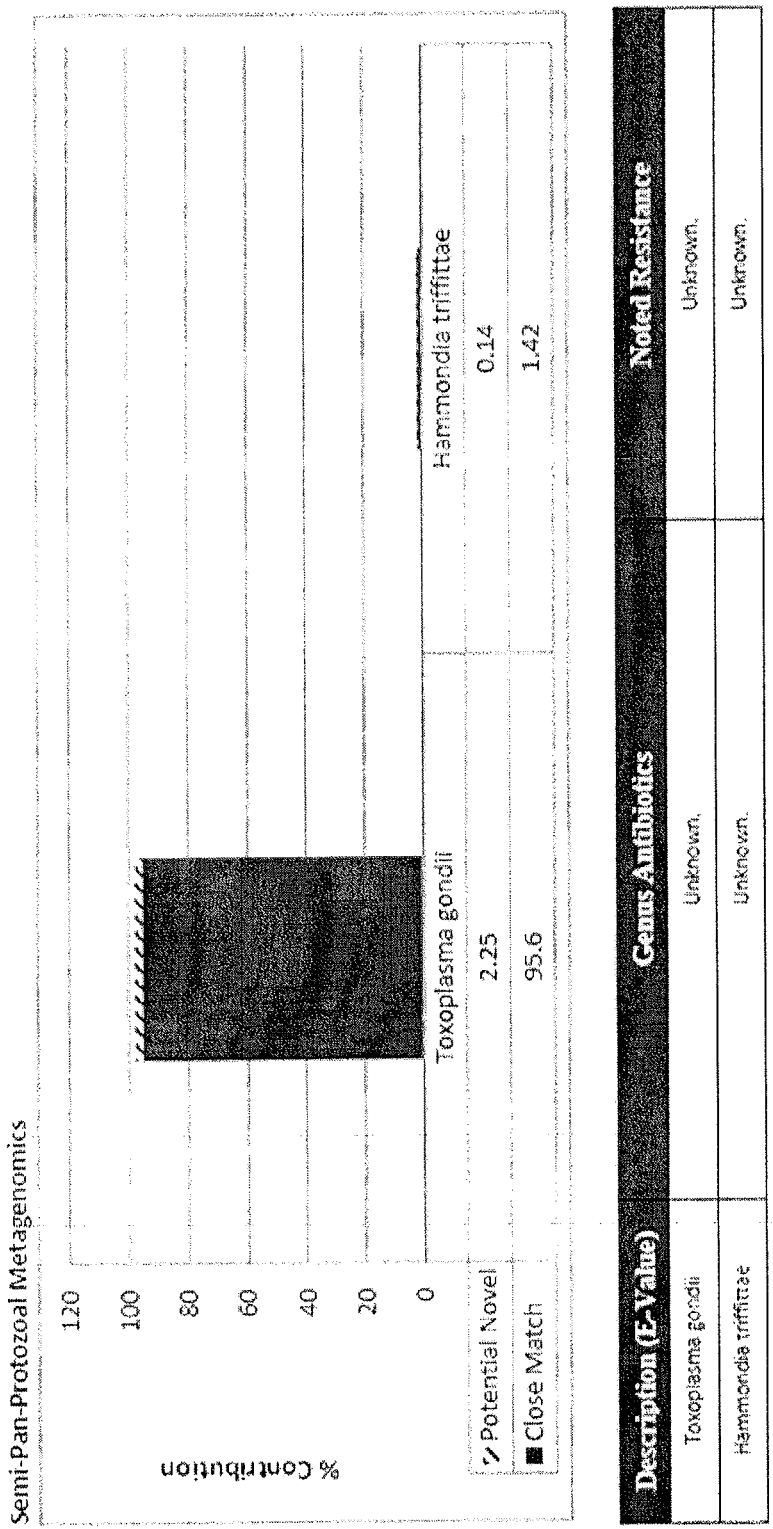
Figure 10:
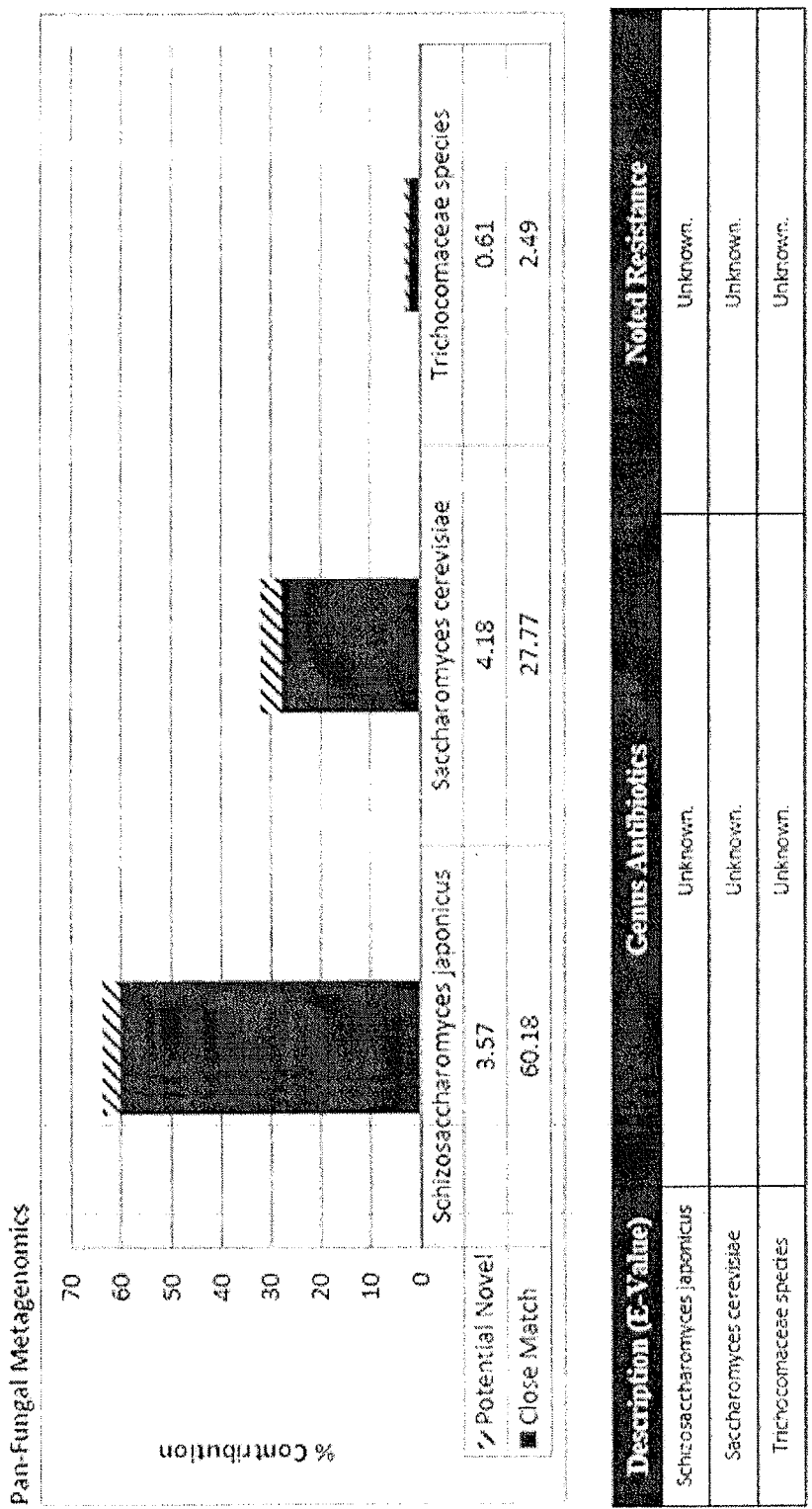

The system can then query a database of treatment information that may contain information such as the treatment (e.g., antibiotic, antiviral, antifungal, antiprotozoal) treatment and sensitivity and/or therapy resistance corresponding to each identified microorganism and the retrieved information may then be used to generate a final report. As shown in FIGS. 5-6, the output of the final report may display information such as, but not limited to: patient information, medical professional information, sample type, collection date, graphical or numerical data relating to one or more characterized or identified microorganisms, a percentage or other numerical indicator of contribution amount of each identified microorganism, a quantitative indicator for a match (e.g., an E-value or % Identity), a description of identified and/or unidentified (novel) microorganisms, and/or treatment sensitivity and/or therapy resistance. Further examples include using the systems, methods and/or kits as described herein to characterize other microorganisms, such as protozoa, viruses, and fungi. FIGS. 7-9 illustrate reports generated from a method that detected protozoa. A PCR procedure suitable for amplification of protozoa is disclosed in application Ser. No. 13/834,441, entitled SEMI-PAN-PROTOZOAL BY QUANTITATIVE PCR, filed on Mar. 15, 2013, the contents of which are hereby incorporated herein by reference, to the extend such contents do not conflict with the present disclosure. FIG. 10 illustrates a report generated from a method that detected fungi. Further, by way of specific example, Adenovirus type 2 was detected using a method as described herein.

It may be advantageous to implement the disclosed system and methods in a language or other format that is compatible with a sequencing platform, such as an ion semiconductor sequencing platform—e.g., an IonTorent Server or an Illumina sequencer, as this may provide added efficiencies to the overall implementation. Additionally, the systems and methods may automatically detect a type of sequence and analyze the sequence information accordingly.

Figure 4:
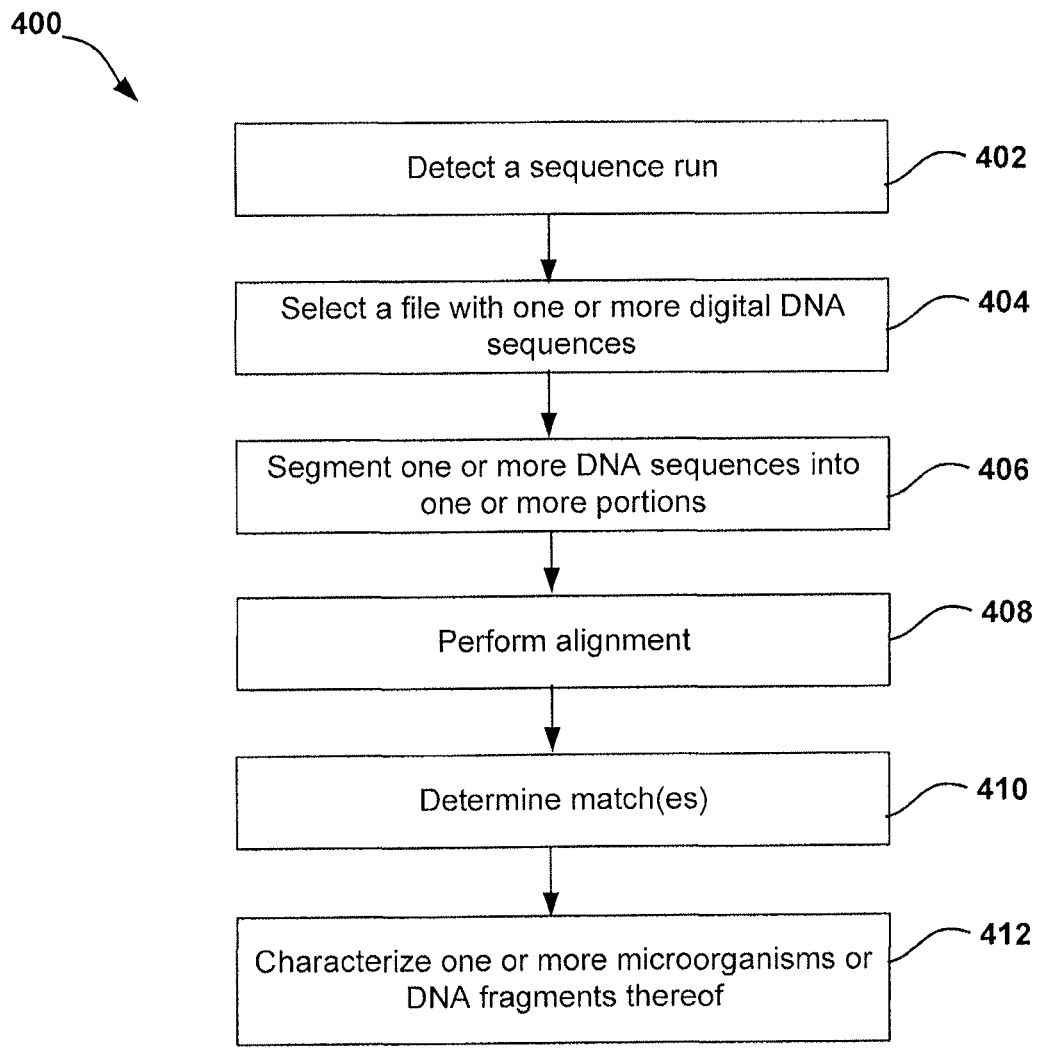
FIG. 4 illustrates another method in accordance with further exemplary embodiments of the disclosure.

Turning now to FIG. 4, a method 400 of automatically characterizing one or more microorganisms is illustrated. Method 400 is similar to method 200, except method 400 includes a step of detecting a sequence run that generates a digital DNA sequence of one or more microorganism (step 402) and does not necessarily, but can, include a performing a set of alignments by comparing the one or more sequence portions to information stored in a second database.

In the illustrated example, method 400 includes the steps of detecting a sequence run that generates a digital DNA sequence of one or more microorganisms (step 402); selecting, by a computer, a digital file comprising one or more digital DNA sequences, wherein each of the one or more digital DNA sequences corresponds to a microorganism to be characterized (step 404); segmenting, by the computer, each of the one or more digital DNA sequences into one or more portions (step 406); performing, by the computer, a set of alignments by comparing the one or more portions to information stored in one or more databases (step 408); determining, by the computer, sequence portions from among the one or more portions that have an alignment match to the information stored in the one or more databases (step 410); and characterizing one or more microorganisms or DNA fragments thereof based on the alignment match (step 412).

Step 402 includes automatically detecting a sequence run that generates a digital DNA sequence of one or more microorganisms. This can be done as described above in connection with process 300. Steps 404-412 can be the same or similar to steps 202-208 and 216 of method 200.

Method 400 can also include steps of optionally further segmenting, by the computer, each of the one or more digital DNA sequences into one or more second portions (wherein the portions noted above become first portions); performing, by the computer, a set of alignments by comparing the one or more first portions or the one or more second portions to information stored in a database (e.g., a second database); and determining, by the computer, sequence portions from among the one or more first portions or the one or more second portions that have an alignment match to the information stored in a database (e.g., the second database). Similar to method 200, these steps can be iteratively repeated with a comparison window decreasing in size with each run. Additional steps noted above in connection with method 200 can also be includes in method 400.

In accordance with various embodiments of the disclosure, method 200 or method 400 can be performed on a computer on a local network. By performing the processing functions of the disclosed systems or methods locally within the system, an Internet connection is not needed to sustain the processing. This offers additional security and reduces networking requirements. Implementations of the disclosed system and method are intended to integrate with existing and future Next Generation Sequencing software platforms such as, for example, Illumina® software applications such as Illumina MiSeq® and Illumina HiSeq®; LifeTechnologies Proton®; LifeTechnologies Personal Genome Machine, and PacBioRS II NGS sequencing systems.

Some specific nonlimiting examples of methods and systems according to the disclosure include the following.

1. A method of characterizing one or more microorganisms, the method comprising the steps of:
   selecting, by a computer, a digital file comprising one or more digital DNA sequences, wherein each of the one or more digital DNA sequences corresponds to a microorganism to be characterized;
   segmenting, by the computer, each of the one or more digital DNA sequences into one or more first portions;
   performing, by the computer, a set of alignments by comparing the one or more first portions to information stored in a first database;
   determining, by the computer, sequence portions from among the one or more first portions that have an alignment match to the information stored in the first database;
   performing, by the computer, a set of alignments by comparing the one or more first portions or the one or more second portions to information stored in a second database;
   determining, by the computer, sequence portions from among the one or more first portions or one or more second portions, wherein the second portions are formed by segmenting, by the computer, each of the one or more digital DNA sequences into one or more second portions, that have an alignment match to the information stored in the second database; and
   characterizing one or more microorganisms or DNA fragments thereof based on the alignment match to the information stored in one or more of the first database and the second database.

2. The method of example 1, wherein the method comprises the steps of:
   performing, by the computer, a set of alignments by comparing the one or more second portions to information stored in at least one database; and
   determining, by the computer, sequence portions from among the one or more second portions that have an alignment match to information stored in the at least one database.

3. The method of example 2, wherein the first portions differ from the second portions.

4. The method of example 2, further comprising:
   further segmenting each of the one or more digital DNA sequences into one or more n portions;
   performing a set of alignments by comparing the one or more n portions to information stored in the at least one database; and
   determining whether any sequence portions from among the one or more n portions have an alignment match to the information stored in the at least one database.

5. The method of example 4, wherein the steps of further segmenting each of the one or more digital DNA sequences into one or more n portions; performing a set of alignments by comparing the one or more n portions to information stored in the at least one database; and determining whether any sequence portions from among the one or more n portions have an alignment match to the information stored in the at least one database are iteratively performed using a comparison window size that decreases as n increases.

6. The method of any of examples 1-5, further comprising the steps of:
   comparing, by the computer, one or more of percentage identity and a sequence E-value corresponding to one or more first portions that do not have an alignment match to information in the first database with one or more of a percentage identity and a sequence E-value corresponding to one or more second portions that do not have an alignment match to information in the second database;
   selecting information stored in the first database or the second database with the highest of one or more of percentage identity and sequence E-value; and characterizing one or more microorganisms or DNA fragments thereof based on the step of selecting information.

7. The method of example 6, further comprising the steps of:
tabulating, by the computer, one or more microorganisms based on the alignment match to the information stored in the first database or the second database and the one or more microorganisms based on the step of selecting information; and
determining a contribution percentage for each of the one or more microorganisms based on the alignment match and the one or more microorganism based on the step of selecting information.

8. The method of any of examples 1-7, further comprising the steps of:
querying, by the computer, a database comprising treatment sensitivity data; and
retrieving, by the computer, treatment sensitivity data corresponding to the one or more microorganisms based on the alignment match to information stored in one or more of the first database and the second database.

9. The method of any of examples 1-8, further comprising a step of generating a report, by the computer, comprising the one or more microorganisms based on the alignment match to the information stored in one or more of the first database and the second database.

10. The method of any of examples 1-9, wherein the method further comprises a step of identifying at least one of the one or more microorganisms.

11. The method of any of examples 1-10, wherein the step of performing, by the computer, a set of alignments by comparing the one or more first portions to information stored in a first database comprises using one or more of BLAST, OTU, G-BLASTN, mpiBLAST, BLASTX, PAUDA, USEARCH, LAST, and BLAT.

12. The method of any of examples 1-11, wherein the step of segmenting, by the computer, each of the one or more digital DNA sequences into one or more first portions comprises segmenting the digital DNA sequence into a first plurality of portions of equal length.

13. The method of any of examples 1-12, wherein the first database comprises a microbial DNA database.

14. The method of any of examples 1-13, wherein the second database comprises a comprehensive nucleic acid database.

15. The method of any of examples 1-14, further comprising a step of detecting, by the computer, an in-process sequence run and querying a server upon completion of the sequence run to retrieve a completed digital file.

16. The method of any of examples 1-15 1, further comprising tabulating only the number of matches for sequences that are among 30% of the longest sequences for which alignments are performed by the computer.

17. The method of any of examples 1-16, further comprising a step of characterizing, by the computer, one or more sequences having one or more of a percentage identity and a sequence E-value that is outside a predetermined range.

18. The method of any of examples 1-17, further comprising a step of displaying information relating to the one or more sequences on a report.

19. A method of automatically characterizing one or more microorganisms, the method comprising the steps of:
detecting a sequence run that generates a digital DNA sequence of one or more microorganisms;
selecting, by a computer, a digital file comprising one or more digital DNA sequences, wherein each of the one or more digital DNA sequences corresponds to a microorganism to be characterized;
segmenting, by the computer, each of the one or more digital DNA sequences into one or more portions;
performing, by the computer, a set of alignments by comparing the one or more portions to information stored in one or more databases;
determining, by the computer, sequence portions from among the one or more portions that have an alignment match to the information stored in the one or more databases; and
characterizing one or more microorganisms or DNA fragments thereof based on the alignment match.

20. The method of example 19, wherein the one or more microorganisms comprises one or more types of microorganisms.

21. A system for computerized microorganism characterization, the system comprising:
a computer configured to:
segment, by the computer, each of the one or more digital DNA sequences into one or more first portions;
perform, by the computer, a set of alignments by comparing the one or more first portions to information stored in a first database;
determine, by the computer, sequence portions from among the one or more first portions that have an alignment match to the information stored in the first database;
perform, by the computer, a set of alignments by comparing the one or more first portions or the one or more second portions to information stored in a second database;
determine, by the computer, sequence portions from among the one or more first portions or one or more second portions that have an alignment match to the information stored in the second database; and
characterize one or more microorganisms or DNA fragments thereof based on the alignment match to the information stored in one or more of the first database and the second database.

22. The system of example 21, wherein the computer is further configured to:
further segment, by the computer, each of the one or more digital DNA sequences into one or more second portions;
perform, by the computer, a set of alignments by comparing the one or more second portions to information stored in at least one database; and
determine, by the computer, sequence portions from among the one or more second portions that have an alignment match to information stored in the at least one database.

23. The system of any of examples 21-22, wherein the second portions are exclusive of the first portions.

24. The system of any of examples 21-23, wherein the first database comprises a microbial DNA database.

25. The system of any of examples 21-24, wherein the second database comprises a comprehensive nucleic acid database.

26. The system of any of examples 21-25, wherein the computer iteratively:
further segments each of the one or more digital DNA sequences into one or more n portions;

performs a set of alignments by comparing the one or more n portions to the information stored in at least one database; and determines whether any sequence portions from among the one or more n portions have an alignment match to the information stored in at least one database.

27. The system of example 24, wherein the computer uses a comparison window size that decreases as n increases.

28. The system of any of examples 21-27, wherein the computer is further configured to generate a report comprising one or more characterized microorganisms and corresponding treatment sensitivity data.

29. The system of any of examples 21-28, further comprising a server configured to store, retrieve, and transmit data from a database comprising treatment sensitivity data corresponding to the one or more characterized microorganisms in response to a query received from the computer.

30. The system of any of examples 21-29, wherein the computer is further configured to detect an in-process sequence run and query a server upon completion of the sequence run to retrieve a completed digital file.

31. The system of any of examples 21-30, wherein the computer is further configured to tabulate only a number of matches for sequences that are among 30% of the longest sequences for which alignments are performed.

32. The system of any of examples 21-31, wherein the computer is further configured to tabulate region information for two or more regions of at least a portion of the one or more digital DNA sequences.

33. The system of any of examples 21-32, wherein the computer is further configured to identify one or more sequences having one or more of a percentage identity and a sequence E-value that is outside a predetermined range.

34. The system of example 31, wherein the computer is further configured to display information relating to the one or more sequences having one or more of a percentage identity and a sequence E-value that is outside a predetermined range.

35. A system for automatic computerized generation of microorganism characterization information, the system comprising:

a computer configured to:
   automatically select a digital file comprising one or more digital DNA sequences, wherein each of the one or more digital DNA sequences corresponds to a microorganism to be characterized;
   segment each of the one or more digital DNA sequences into one or more portions;
   perform a set of alignments by comparing the one or more portions to information stored in one or more databases;
   determine sequence portions from among the one or more portions that have an alignment match to the information stored in the one or more databases; and
   characterize one or more microorganisms or DNA fragments thereof based on the alignment match.

Exemplary methods of the present disclosure described above may be implemented as one or more software processes executable by one or more processors and/or one or more firmware applications. The processes and/or firmware are configured to operate on one or more general purpose microprocessors or controllers, a field programmable gate array (FPGA), an application specific integrated circuit (ASIC), or other hardware capable of performing the actions describe above. In an exemplary embodiment of the present disclosure, software processes are executed by a CPU in order to perform the actions of the present disclosure.

Additionally, the present disclosure is not described with reference to any particular programming language. It will be appreciated that a variety of programming languages may be used to implement the teachings of the disclosure as described herein.

The methods herein may be employed with any form of memory device including all forms of sequential, pseudo-random, and random access storage devices. Storage devices as known within the current art include all forms of random access memory, magnetic and optical tape, magnetic and optical disks, along with various other forms of solid-state mass storage devices. The current disclosure applies to all forms and manners of memory devices including, but not limited to, storage devices utilizing magnetic, optical, and chemical techniques, or any combination thereof.

In places where the description above refers to particular implementations of computerized microorganism identification systems and methods, it should be readily apparent that a number of modifications may be made without departing from the spirit thereof and that these implementations may be applied to other embodiments of computerized microorganism identification systems and methods.

What is claimed is:

1. A method comprising:

accessing, at a computer system, a plurality of DNA sequence data sets that correspond to a particular biological sample;

identifying, based on lengths of the plurality of DNA sequence data sets, an incomplete subset of the plurality of DNA sequence data sets;

performing, for each DNA sequence data set in the incomplete subset, a multi-pronged assessment of potential alignments for the DNA sequence data set by:

generating, by the computer system, one or more first alignment results for the DNA sequence data set by comparing the DNA sequence data set to each of one or more first reference data sets stored in a first database, wherein, for a DNA sequence data set in the incomplete subset, comparing the DNA sequence data set to each of the one or more first reference data sets is performed using a first window size;

determining, based on the one or more first alignment results, whether a predetermined match condition is satisfied;

when it is determined that a predetermined match condition is not satisfied:

generating a plurality of second alignment results for the DNA sequence data set by comparing the DNA sequence data set to each of a plurality of second reference data sets stored in a second database;

comparing at least one of the one or more first alignment results with at least one of the plurality of second alignment results, wherein, for a particular DNA sequence data set in the incomplete subset, comparing the DNA sequence data set to each of the plurality of the second reference data sets is performed using a second window size, the first window size being smaller than the second window size; and selecting, based on the comparison, a particular reference data set to associate with the DNA sequence data set, the particular reference data set being one of the one or more first reference data sets associated with the first database or one of the plurality of second reference data sets associated with the second database; and identifying a microorganism to associate with the DNA sequence data set based on the particular reference data set;

identifying, for each microorganism associated with any of the incomplete subset, a quantity of DNA sequence data sets within the incomplete subset associated with the microorganism;

determining, based on the quantities, two or more microorganisms to associate with the particular biological sample; and outputting an identification of the two or more microorganisms.

2. The method of claim 1, wherein determining whether a predetermined match condition is satisfied includes:

determining whether any of the one or more first alignment results indicates that a corresponding first reference data set of the one or more first reference data sets matches the DNA sequence data set within a predetermined tolerance.

3. The method of claim 1, wherein:

each first alignment result of the one or more first alignment results is generated based on an extent to which at least part of the DNA sequence data set is the same as at least part of a first reference data set of the one or more first reference data sets.

4. The method of claim 1, further comprising, for each DNA sequence data set in the incomplete subset:

segmenting the DNA sequence data set to produce multiple portions of the DNA sequence data set using a window of a window size, wherein generating the one or more first alignment results includes:

comparing, for each portion of the multiple portions of the DNA sequence data set, the portion to each of the one or more first reference data sets.

5. The method of claim 1, further comprising, for the particular DNA sequence data set of the incomplete subset or for another particular DNA sequence data set of the incomplete subset:

segmenting, using a window of a window size, the DNA sequence data set to produce multiple portions of the DNA sequence data set, wherein comparing the DNA sequence data set to each of the plurality of the one or more first reference data sets includes comparing each of the multiple portions to the each of the one or more first reference data sets.

6. The method of claim 1, wherein identifying the incomplete subset includes:

defining the incomplete subset to include each DNA sequence data set of the plurality of DNA sequence data sets that has a sequence length that is at least as long as a predefined threshold sequence length.

7. The method of claim 1, wherein identifying the incomplete subset includes:

identifying a predefined percentage of the plurality of DNA sequence data sets that represent the longest sequence lengths within the plurality of DNA sequence data sets.

8. A system comprising:

one or more data processors; and a non-transitory computer readable storage medium containing instructions which when executed on the one or more data processors, cause the one or more data processors to perform actions including:

accessing, at a computer system, a plurality of DNA sequence data sets that correspond to a particular biological sample;

identifying, based on lengths of the plurality of DNA sequence data sets, an incomplete subset of the plurality of DNA sequence data sets;

performing, for each DNA sequence data set in the incomplete subset, a multi-pronged assessment of potential alignments for the DNA sequence data set by:

segmenting, using a window of a window size, the DNA sequence data set to produce multiple portions of the DNA sequence data set;

generating, by the computer system, one or more first alignment results for the DNA sequence data set by comparing the DNA sequence data set to each of one or more first reference data sets stored in a first database, wherein comparing the DNA sequence data set to each of the plurality of the one or more first reference data sets includes comparing each of the multiple portions to the each of the one or more first reference data sets;

determining, based on the one or more first alignment results, whether a predetermined match condition is satisfied;

when it is determined that a predetermined match condition is not satisfied:

generating a plurality of second alignment results for the DNA sequence data set by comparing the DNA sequence data set to each of a plurality of second reference data sets stored in a second database;

comparing at least one of the one or more first alignment results with at least one of the plurality of second alignment results; and selecting, based on the comparison, a particular reference data set to associate with the DNA sequence data set, the particular reference data set being one of the one or more first reference data sets associated with the first database or one of the plurality of second reference data sets associated with the second database; and identifying a microorganism to associate with the DNA sequence data set based on the particular reference data set;

identifying, for each microorganism associated with any of the incomplete subset, a quantity of DNA sequence data sets within the incomplete subset associated with the microorganism;

determining, based on the quantities, two or more microorganisms to associate with the particular biological sample; and outputting an identification of the two or more microorganisms.

9. The system of claim 8, wherein determining whether a predetermined match condition is satisfied includes:

determining whether any of the one or more first alignment results indicates that a corresponding first reference data set of the one or more first reference data sets matches the DNA sequence data set within a predetermined tolerance.

10. The system of claim 8, wherein:

each second alignment result of the plurality of second alignment results is generated based on an extent to which at least part of the DNA sequence data set is the same as at least part of a second reference data set of the plurality of second reference data sets.

11. The system of claim 8, wherein, for a particular DNA sequence data set in the incomplete subset:

comparing the DNA sequence data set to each of the one or more first reference data sets is performed using a first window size; and comparing the DNA sequence data set to each of the plurality of the second reference data sets is performed using a second window size, the first window size being smaller than the second window size.

12. The system of claim 8, wherein identifying the incomplete subset includes:

defining the incomplete subset to include each DNA sequence data set of the plurality of DNA sequence data sets that has a sequence length that is at least as long as a predefined threshold sequence length.

13. The system of claim 8, wherein identifying the incomplete subset includes:

identifying a predefined percentage of the plurality of DNA sequence data sets that represent the longest sequence lengths within the plurality of DNA sequence data sets.

14. A computer-program product tangibly embodied in a non-transitory machine-readable storage medium, including instructions configured to cause one or more data processors to perform actions including:

accessing, at a computer system, a plurality of DNA sequence data sets that correspond to a particular biological sample;

identifying, based on lengths of the plurality of DNA sequence data sets, an incomplete subset of the plurality of DNA sequence data sets;

performing, for each DNA sequence data set in the incomplete subset, a multi-pronged assessment of potential alignments for the DNA sequence data set by:

segmenting, using a window of a window size, the DNA sequence data set to produce multiple portions of the DNA sequence data set;

generating, by the computer system, one or more first alignment results for the DNA sequence data set by comparing the DNA sequence data set to each of one or more first reference data sets stored in a first database, wherein comparing the DNA sequence data set to each of the plurality of the one or more first reference data sets includes comparing each of the multiple portions to the each of the one or more first reference data sets;

determining, based on the one or more first alignment results, whether a predetermined match condition is satisfied;

when it is determined that a predetermined match condition is not satisfied:

generating a plurality of second alignment results for the DNA sequence data set by comparing the DNA sequence data set to each of a plurality of second reference data sets stored in a second database;

comparing at least one of the one or more first alignment results with at least one of the plurality of second alignment results; and selecting, based on the comparison, a particular reference data set to associate with the DNA sequence data set, the particular reference data set being one of the one or more first reference data sets associated with the first database or one of the plurality of second reference data sets associated with the second database; and identifying a microorganism to associate with the DNA sequence data set based on the particular reference data set;

identifying, for each microorganism associated with any of the incomplete subset, a quantity of DNA sequence data sets within the incomplete subset associated with the microorganism;

determining, based on the quantities, two or more microorganisms to associate with the particular biological sample; and outputting an identification of the two or more microorganisms.

15. The computer-program product of claim 14, wherein:

each second alignment result of the plurality of second alignment results is generated based on an extent to which at least part of the DNA sequence data set is the same as at least part of a second reference data set of the plurality of second reference data sets.

16. The computer-program product of claim 14, wherein identifying the incomplete subset includes:

defining the incomplete subset to include each DNA sequence data set of the plurality of DNA sequence data sets that has a sequence length that is at least as long as a predefined threshold sequence length.

17. The computer-program product of claim 14, wherein identifying the incomplete subset includes:

identifying a predefined percentage of the plurality of DNA sequence data sets that represent the longest sequence lengths within the plurality of DNA sequence data sets.

* * * * *